United States Patent
Fernandez-Cuesta et al.

(10) Patent No.: US 9,829,425 B2
(45) Date of Patent: Nov. 28, 2017

(54) OPTOFLUIDIC DEVICES AND METHODS FOR SENSING SINGLE PARTICLES

(71) Applicants: Irene Fernandez-Cuesta, San Francisco, CA (US); Stefano Cabrini, Albany, CA (US)

(72) Inventors: Irene Fernandez-Cuesta, San Francisco, CA (US); Stefano Cabrini, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/253,051

(22) Filed: Apr. 15, 2014

(65) Prior Publication Data

US 2014/0313507 A1    Oct. 23, 2014

Related U.S. Application Data

(60) Provisional application No. 61/814,484, filed on Apr. 22, 2013.

(51) Int. Cl.
*G01N 15/14* (2006.01)
*G01N 21/05* (2006.01)
(Continued)

(52) U.S. Cl.
CPC .... *G01N 15/1459* (2013.01); *B01L 3/502707* (2013.01); *G01N 15/1434* (2013.01);
(Continued)

(58) Field of Classification Search
CPC ............... G01N 21/648; G01N 21/658; G01N 15/1459; G01N 15/1434; G01N 15/1484; G01N 2012/6439; G01N 2015/0038; G01N 15/14; B01L 3/502707; B01L 3/502761; B01L 2200/0663; B01L 2300/0877; B01L 2300/0896
(Continued)

(56) References Cited

U.S. PATENT DOCUMENTS

| | | | | |
|---|---|---|---|---|
| 6,894,359 | B2 * | 5/2005 | Bradley et al. | B82Y 15/00 257/253 |
| 7,290,667 | B1 * | 11/2007 | Bakajin et al. | B01D 39/06 210/500.22 |

(Continued)

OTHER PUBLICATIONS

Alexandre G. Brolo, Plasmonics for future biosensors, Nature Photonics 6, 709-713 (2012).
(Continued)

*Primary Examiner* — Sang Nguyen (57) ABSTRACT

This disclosure provides systems, methods, and apparatus related to optofluidic devices. In one aspect, an optofluidic device includes a substrate, a first nanostructure, a second nanostructure, and a cover. A channel having cross-sectional dimensions of less than about 100 nanometers is defined in a surface of the substrate. The first nanostructure is disposed on the substrate on a first side of the channel and proximate the channel. The second nanostructure is disposed on the substrate on a second side of the channel and proximate the channel. The first and the second nanostructures are disposed on a line that passes across the channel. The cover is disposed on the surface of the substrate.

16 Claims, 7 Drawing Sheets

(51) Int. Cl.
*G01N 21/64* (2006.01)
*G01N 21/65* (2006.01)
*B01L 3/00* (2006.01)
*G01N 15/00* (2006.01)

(52) U.S. Cl.
CPC ....... *G01N 15/1484* (2013.01); *G01N 21/648* (2013.01); *G01N 21/658* (2013.01); *B01L 3/502761* (2013.01); *B01L 2200/0663* (2013.01); *B01L 2300/0877* (2013.01); *B01L 2300/0896* (2013.01); *G01N 2015/0038* (2013.01); *G01N 2021/6439* (2013.01)

(58) Field of Classification Search
USPC .................................. 356/244, 246, 300–301
See application file for complete search history.

(56) References Cited

U.S. PATENT DOCUMENTS

| | | | | |
|---|---|---|---|---|
| 8,436,990 | B2* | 5/2013 | Matsumoto et al. | B01L 3/502715 356/244 |
| 8,564,781 | B2* | 10/2013 | Miyadera et al. | G01N 21/553 356/445 |
| 2003/0209314 | A1* | 11/2003 | Guo et al. | B01L 3/502707 156/247 |
| 2007/0122313 | A1* | 5/2007 | Li et al. | B81C 1/00071 422/400 |
| 2008/0135826 | A1* | 6/2008 | Fonash et al. | B81C 1/0019 257/9 |
| 2008/0221806 | A1* | 9/2008 | Bryant et al. | G01N 27/127 702/22 |
| 2011/0116093 | A1* | 5/2011 | Liu et al. | G01N 21/0303 356/432 |
| 2011/0166045 | A1* | 7/2011 | Dhawan et al. | B82Y 10/00 506/39 |
| 2011/0174069 | A1* | 7/2011 | Cornelius et al. | B01J 19/0093 73/204.23 |
| 2012/0134880 | A1* | 5/2012 | Kurkina et al. | G01N 27/4146 422/82.01 |

OTHER PUBLICATIONS

Irene Fernandez-Cuesta et al., Fabrication of fluidic devices with 30nm nanochannels by direct imprinting, J. Vac. Sci. Technol. B 29, 06F801 (2011).

Roxworthy, B. J., et al., "Application of Plasmonic Bowtie Nanoantenna Arrays for Optical Trapping, Stacking, and Sorting," Nano Lett. 2012, 12, 796-801.

Kinkhabwala, A., et al., "Large single-molecule fluorescence enhancements produced by a bowtie nanoantenna," Nature Photonics, vol. 3, Nov. 2009, 654-657.

Schuck, P.J., et al., "Improving the Mismatch between Light and Nanoscale Objects with Gold Bowtie Nanoantennas," PRL 94, 017402 (2005).

Hatab, N.A., "Free-Standing Optical Gold Bowtie Nanoantenna with Variable Gap Size for Enhanced Raman Spectroscopy," Nano Lett. 2010, 10, 4952-4955.

* cited by examiner

OPTOFLUIDIC DEVICES AND METHODS FOR SENSING SINGLE PARTICLES

RELATED APPLICATIONS

This application claims priority to U.S. Provisional Patent Application No. 61/814,484, filed Apr. 22, 2013, which is herein incorporated by reference.

STATEMENT OF GOVERNMENT SUPPORT

This invention was made with government support under Contract No. DE-AC02-05CH11231 awarded by the U.S. Department of Energy. The government has certain rights in this invention.

TECHNICAL FIELD

This disclosure relates generally to optofluidic devices and more particularly to optofluidic devices capable of sensing single particles and molecules.

BACKGROUND

Since the 1990s, many techniques for probing individual molecules have been developed. Below is a short summary of such techniques.

Fluorescence—many researchers use fluorescent labels specifically attached to molecules for tracking them by scanning techniques (e.g., confocal microscopy) or by observing them under a fluorescent microscope (e.g., using a microfluidic channel).

Raman spectroscopy—this is a method that gives chemical information about a molecule (i.e., a "molecular fingerprint"), but needs to be combined with plasmonic substrates for studying signals from single molecules (i.e., SERS: Surface Enhanced Raman Spectroscopy). These molecules need to be localized first by other methods (e.g., scanning techniques), immobilized, and the signal acquired for a long period of time.

High resolution microscopy—Scanning probe microscopes (e.g., Atomic Force Microscopes, Scanning Tunnel Microscopes, Near-field Scanning Optical Microscopes) or other high resolution microscopy techniques (e.g., Scanning Electron Microscopy, Transmission Electron Microscopy) can be used to study the topography of molecules or their mechanical properties. These techniques, however, may be destructive, slow, and give very little or no information that may be used to identify the molecules.

All of the above-listed techniques generally are slow and time consuming, use bulky equipment (e.g., optical or electronic microscopes, optical benches, etc.), all generally require complex sample preparation and scanning methods, and both the experiments and data interpretation need be carried out by one trained in the technique. Other drawbacks include the lack of throughput and poor versatility.

SUMMARY

Some embodiments disclosed herein are directed to optofluidic devices that can detect, identify, and count single particles or molecules, one-by-one, in real-time. In some embodiments, an optofluidic device may be able to simultaneously confine light and a liquid down to about a sub-50 nanometer (nm) length scale. Methods of fabrication (e.g., based on high throughput, wafer-scale techniques) and methods of use are also disclosed.

One innovative aspect of the subject matter described in this disclosure can be implemented a device including a substrate, a first nanostructure, a second nanostructure, and a cover. A channel having cross-sectional dimensions or both cross-sectional dimensions of less than about 100 nanometers is defined in a surface of the substrate. The first nanostructure is disposed on the substrate on a first side of the channel and proximate the channel. The second nanostructure is disposed on the substrate on a second side of the channel and proximate the channel. The first and the second nanostructures are disposed on a line that passes across the channel. The cover is disposed on the surface of the substrate.

In some embodiments, the substrate further defines a first nanostructure recess and a second nanostructure recess in the surface of the substrate. The first nanostructure is disposed in the first nanostructure recess, and the second nanostructure is disposed in the second nanostructure recess. In some embodiments, a surface of the channel defines a first plane. A surface of the first nanostructure recess and a surface of the second nanostructure recess define a second plane, with the first plane being substantially in the second plane. In some embodiments, the first and the second nanostructure recesses have a depth of about 10 nanometers to 100 nanometers in the surface of the substrate.

In some embodiments, dimensions of the first and the second nanostructures substantially parallel to the surface of the substrate are less than about 200 nanometers. In some embodiments, the line that passes across the channel is substantially perpendicular to a length of the channel.

In some embodiments, the device further comprises a third nanostructure and a fourth nanostructure disposed on the substrate. The third nanostructure is on the first side of the channel and proximate the channel. The fourth nanostructure is on the second side of the channel and proximate the channel. The third nanostructure and the fourth nanostructure are on a second line that passes across the channel.

In some embodiments, the first and the second nanostructures comprise a metal. In some embodiments, the first and the second nanostructures comprise a metal selected from the group consisting of gold, silver, aluminum, platinum, titanium, chromium, and copper.

In some embodiments, the first and the second nanostructures are operable to support surface plasmons. The surface plasmons are operable to resonate and to generate a region of high electromagnetic field intensity between the first nanostructure and the second nanostructure.

In some embodiments, the first nanostructure is positioned about 1 nanometer to 20 nanometers from the first side of the channel, and the second nanostructure is positioned about 1 nanometer to 20 nanometers from the second side of the channel. In some embodiments, the channel has a width on the surface of the substrate of less than about 100 nanometers, and the first and the second nanostructures are separated from each other by at least the width of the channel. In some embodiments, the channel has a depth in the substrate of less than about 100 nanometers.

In some embodiments, the substrate comprises a polymer. In some embodiments, a length of the channel is about 1 micron to 200 microns. In some embodiments, the cover comprises a polymer or a glass.

In some embodiments, the device further comprises a second channel defined in the surface of the substrate and coupled to the channel, with the cover defining a hole, and the hole being coupled to the second channel and providing an inlet for a liquid to the device. In some embodiments, the device further comprises a second channel defined in the surface of the substrate and coupled to the channel, with the substrate defining a hole, and the hole being coupled to the second channel and providing an inlet for a liquid to the device.

Another innovative aspect of the subject matter described in this disclosure can be implemented a method including providing a device. The device includes a substrate, a first nanostructure, a second nanostructure, and a cover. A channel is defined in a surface of the substrate. The first nanostructure is disposed on the substrate on a first side of the channel and proximate the channel. The second nanostructure is disposed on the substrate on a second side of the channel and proximate the channel. The first and the second nanostructures are disposed on a line that passes across the channel. A cover is disposed on a surface of the substrate. A liquid including a plurality of particles is provided to the channel of the device. The first and the second nanostructures of the device are illuminated with electromagnetic radiation of specific wavelengths or a specific wavelength. A characteristic of a single particle of the plurality of particles is measured, as the single particle flows in the channel past the first and the second nanostructures, from the interaction of the single particle with a region of high electromagnetic field intensity between the first nanostructure and the second nanostructure.

Another innovative aspect of the subject matter described in this disclosure can be implemented a method including fabricating a fluidic device including substrate having a surface defining a channel, a first nanostructure recess on a first side of the channel and proximate the channel, and a second nanostructure recess on a second side of the channel and proximate the channel. A sacrificial metal is deposited on the surface of the fluidic device without substantially depositing the sacrificial metal in the first nanostructure recess or the second nanostructure recess. A device metal is deposited on the sacrificial metal and in the first and the second nanostructure recesses. The sacrificial metal is removed. In some embodiments, device metal overlying the sacrificial metal is removed.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

Introduction

Detecting and identifying a single molecule represents the ultimate sensitivity in chemical and biochemical analyses. This is a technological challenge that is attracting the attention of many researchers from many disciplines due to its scientific implications. The methods currently used to characterize single molecules are rudimentary and suitable for basic research purposes. There are no techniques, however, that allow for the characterization of single molecules with a reasonable throughput; these types of analyses are currently performed using bulky, expensive, and complex equipment in which slow and time-consuming experiments are performed.

Research has been focused on overcoming or partially solving some of the issues with current techniques by integrating different functionalities within the same device (i.e., the so called "lab-on-a-chip") that allow new capabilities that are not otherwise possible. An example of a "lab-on-a-chip" is an optofluidic device that combines microfluidics with optical excitation and/or transduction. The use of a microchannel (i.e., a channel having cross-sectional dimensions on the order of microns to hundreds of microns or having a hydraulic diameter below about 1 millimeter) in an optofluidic device facilitates the delivery and control of an analyte to an area under study, and allows for the integration of multiple functionalities, miniaturization, and portability. The use of optical signals in an optofluidic device allows for fast excitation and read-out, and may be non-destructive. The use of plasmonic structures in an optofluidic device goes further, as plasmonic structures can enable light manipulation beyond the diffraction limit and can enhance optical signals (e.g., fluorescence or Raman) by several orders of magnitude. A brief overview of the use of plasmonics for sensing can be found in "Plasmonics for future biosensors" by Alexandre G. Brolo, Nature Photonics 6, 709-713 (2012), which is herein incorporated by reference.

Some research regarding integrating plasmonic substrates with microfluidics has shown promising results for low analyte concentrations. Measurements, however, may still require sample preparation (e.g., drying or pre-concentration near the sensitive area) and are far from achieving single molecule detection. Detection of high analyte concentrations can be difficult due to the presence of several particles in the diffraction limited light spot at the same time. A device that can be used for both low and high sample concentrations has not been developed.

Most of current plasmonic-based optofluidic devices use large-area plasmonic substrates (e.g., large arrays of antennas, pillars, or holes) inside a microfluidic channel. In these devices, the read-out signal is an average from many plasmonic structures from a micron-sized spot (e.g., from a laser), which limits the sensitivity of such devices. Further, the size mismatch between the sensitive area/hot spots of the plasmonic structures and the size of the fluidic channel may make a measurement dependent on diffusion in a way in which not all the substance is analyzed, which further limits the sensitivity and throughput. One outstanding challenge in combining plasmonics and fluidics is the placement of a single target molecule at one hot spot of a plasmonic structure, and reading the signal from the single target molecule.

As described herein, a nanochannel is a channel having cross-sectional dimensions on the order of nanometers to tens of nanometers. For example, if a nanochannel has a circular cross section, the diameter of the cross section of the nanochannel would be on the order of nanometers to tens of nanometers. As another example, if a nanochannel has a square or rectangular cross section, the sides of the cross section of the nanochannel would be on the order of nanometers to tens of nanometers.

A nanochannel with about the same dimensions as a plasmonic nano-antenna hot spot may be used to deliver molecules or particles of a sample, one-by-one, into the plasmonic hot spot. At the plasmonic hot spot, the molecules can be detected and analyzed. Using one plasmonic nano-antenna instead of a large area substrate may allow for confining and focusing of the optical field into a nanometric spot, where the optical field is strong and which is not size-limited by light diffraction. This implies high sensitivity and spatial resolution.

Thus, an optofluidic device, incorporating a nano-antenna and a nanochannel, may allow for high sensitivity, down to the single molecule level. In addition, such a device may aid in ensuring that all of the molecules that pass through or that are inserted in the device are sensed, yielding high accuracy and throughput. In some embodiments, for improved analysis speed, multiple nano-antennas and nanochannels can be placed in the same device (e.g., several thousand nano-antennas coupled to corresponding nanochannels) at little to no extra cost, since the fabrication process can be parallel and wafer-scale.

Plasmonic Nanostructures

Some nanostructures (e.g., metal nanostructures) can support localized surface plasmon resonances. In certain configurations, some nanostructures can generate confined electromagnetic fields where the incident electromagnetic field is enhanced by several orders of magnitude (i.e., hot spots). The plasmonic resonances observed in such nanostructures can be used to create antennas (i.e., a nano-antenna) that can operate in the visible and part of the near infrared spectrum (e.g., about 390 nanometers (nm) to 900 nm). Some examples of optical nano-antennas are paired metallic nanostructures, metal strips, nanorods, bowtie-shaped structures, nano-discs, and nano-spheres. In some embodiments, dipole or bowtie-shaped nano-antennas may combine the formation of a strong hot spot in the gap of the nano-antenna and the tunability of the resonance of the nano-antenna.

Some properties that make plasmonic nano-antennas useful for high sensitivity sensors include: (i) nano-antennas show a well-defined resonance for a given geometry and excitation conditions (i.e., when the geometry and excitation conditions change, the resonant peak changes); (ii) the resonance can be tuned by changing the nano-antenna geometry or material, and the optimal wavelength range can be tailored to match the specific application; (iii) plasmonic structures enhance the optical fields that match their resonant range in several orders of magnitude; for optical spectroscopy under certain conditions, this enhancement can be doubled, with both the excitation and emitted signals being enhanced, meaning a squared total enhancement factor; (iv) plasmonic nano-antennas can confine optical fields down to the nanometer scale—i.e., they can "nano-focus" light with an advantage that the size of this localized hot spot is not limited by light diffraction, and is given by the structure geometry.

Nanochannels and Microfluidic Systems

A nanochannel (e.g., a channel in a substrate that has a width and a height (or a depth) under about 100 nm) can confine a sample volume to the zeptoliter (zL) range. In such a sample volume, one specific type of particle (e.g., molecule or nanoparticle) may be able to pass through the nanochannel at a time. The nanochannel dimensions and its surface properties can be altered or changed to fit individual particles of different types and sizes.

A nanochannel may be integrated in a microfluidic device/chip. Microfluidic devices can control liquid/sample movement and analyte delivery on-chip, and allow for the integration of many functionalities such as filtering, separation, particle sorting, pumping, and energy generation. In addition, microfluidic systems may permit work with bio-molecules in their natural environment, which may reduce or minimize sample preparation and may not impose limits in the study of living or buffer-sensitive entities. Further, surface chemistry (e.g., silanization or thiolization) can be used to make the nanochannels and microchannels of a microfluidic device selectively permeable to some liquids, to trap or immobilize molecules, to induce reactions, to reduce the flow rate, etc.

A microfluidic device can be connected to a macroscopic system (e.g., a peristaltic pump, a syringe, or an electrophoresis system) for liquid input and control. With the microfluidic device connected to a macroscopic system, it may be possible to select and control molecules to be delivered to a specific nanochannel.

Devices

As described herein, an optofluidic device may allow for the spatial confinement of light and a liquid, simultaneously, into a few tens of nanometers. A nanochannel can be adjusted to accommodate a specific type of particle, molecule, or biomolecule. This may allow for the detection of single molecules that pass one-by-one along the nanochannel into a plasmonic hot spot in a controlled fashion. The analyte flow may be controlled by a complete microfluidic system; the microfluidic system can incorporate many other functionalities that may be used for liquid manipulation.

Figure 1:
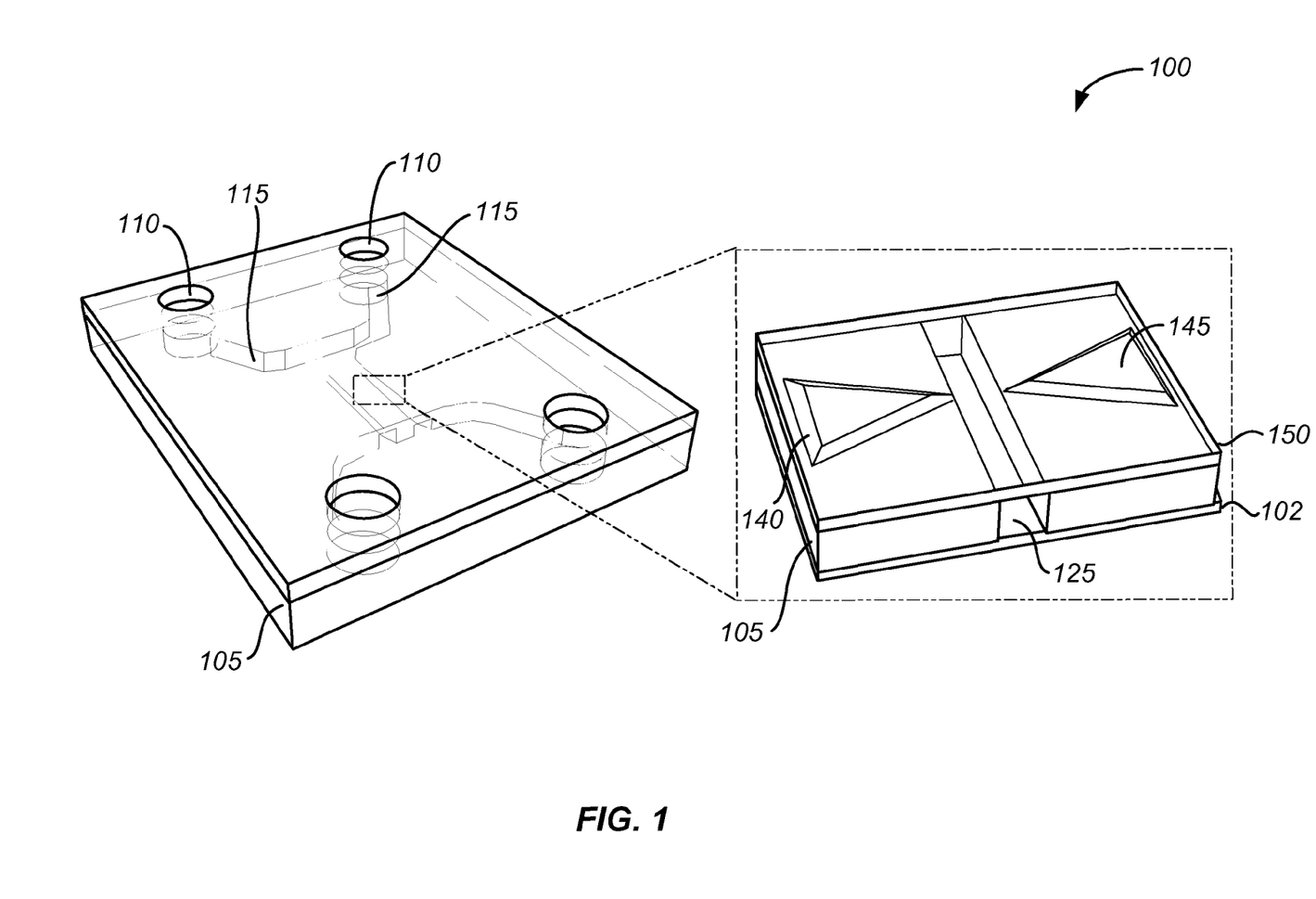
FIG. 1 shows an example of an isometric illustration of an optofluidic device.
Figure 2:
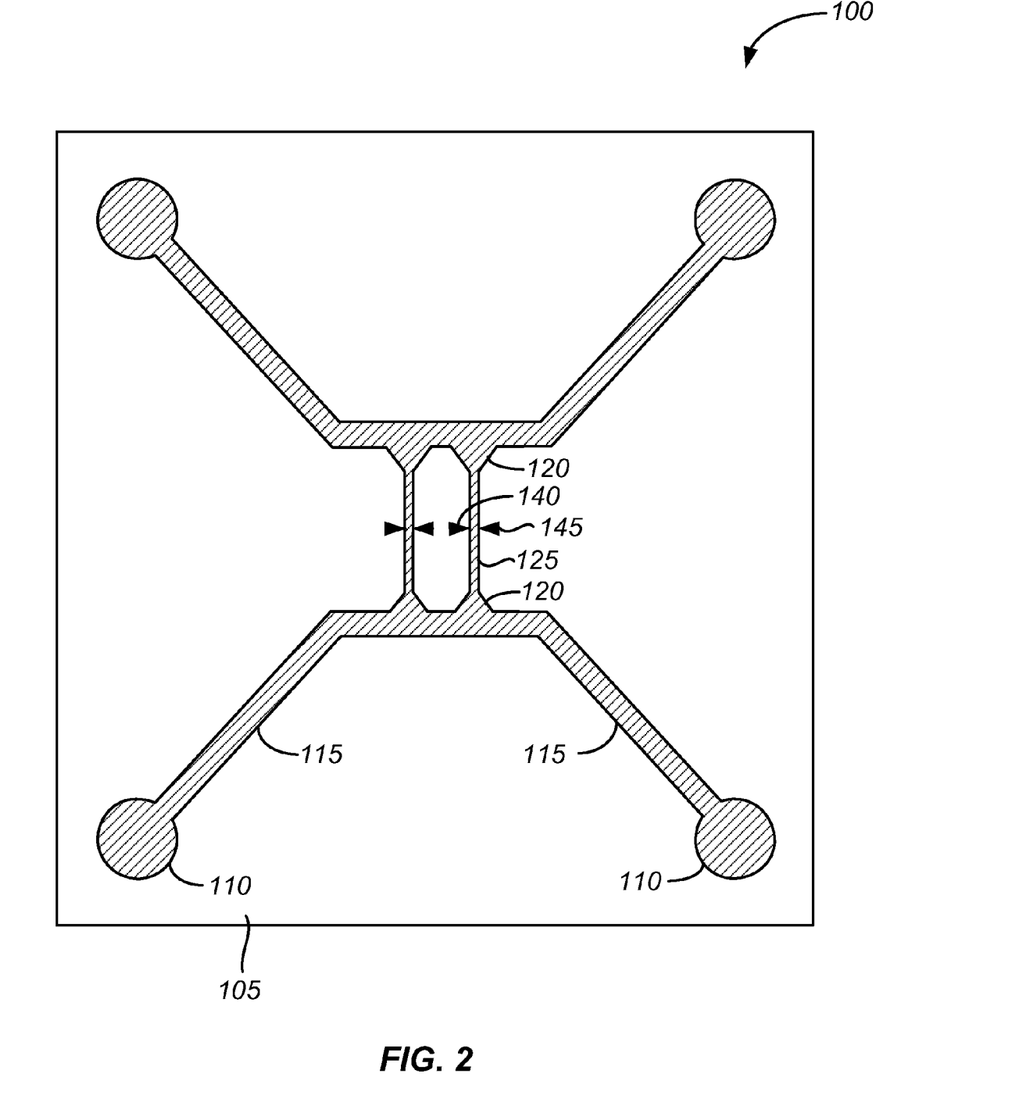
FIG. 2 shows an example of a top-down illustration of features defined by the substrate of the optofluidic device shown in FIG. 1.

FIG. 1 shows an example of an isometric illustration of an optofluidic device. FIG. 2 shows an example of a top-down illustration of features defined by the substrate of the optofluidic device shown in FIG. 1. As shown in FIGS. 1 and 2, an optofluidic device 100 includes a substrate 105 which has a number of features defined in it, including reservoirs 110, microchannels 115, inlets 120, and nanochannels 125. In some embodiments, the substrate 105 may comprise a polymer. In some embodiments, the substrate may be disposed on a substrate carrier 102. In some embodiments, the substrate carrier 102 may comprise a polymer, a glass, or a semiconductor (e.g., silicon). The reservoirs 110 are connected to the microchannels 115. The microchannels 115 are connected to the nanochannels 125 by the inlets 120. A cover 150 is disposed on substrate 105 to enclose the reservoirs 110, the microchannels 115, the inlets 120, and the nanochannels 125. In some embodiments, the cover may comprise a polymer or a glass.

The features in the substrate 105 are operable to provide control of a liquid and may be used to filter, sort, mix, and separate different liquids. In some embodiments, the features in the substrate 105 may form parts of microfluidic device. The optofluidic device 100 may be coupled or connected to a macroscopic system that is operable to control the flow of liquids (and particles in the liquids) through the channels of the optofluidic device 100. For example, a macroscopic system may include controllers or feedback controllers that may direct a liquid in the optofluidic device 100 and may separate particles and direct the particles to different nanochannels for detection and/or identification.

In some embodiments, a reservoir 110 may be used as an entry point for liquids to the optofluidic device 100. For example, a portion of the cover 150 overlying a reservoir 110 may define a hole that allows access to a microchannel. As another example, a portion of the substrate 105 and a portion of the substrate carrier 102 may define a hole that allows access to a microchannel. In some embodiments, a reservoir 110 may be used as a pathway to apply pressure or a voltage to the fluid in the optofluidic device 100.

In some embodiments, the inlets 120 may be tapered. In some embodiments, the inlets 120 may be tapered in two dimensions or in three dimensions. In some embodiments, a tapered inlet may allow particles to more easily flow into a nanochannel 125. In some embodiments, a tapered inlet may be configured (e.g., have a certain size or a certain shape) so that a specific particle may flow from a microchannel 115 to a nanochannel 125.

In some embodiments, a nanochannel may have a square or a rectangular cross section. In some embodiments, a nanochannel may have cross-sectional dimensions of less than about 100 nm. For example, when the nanochannel has a square or a rectangular cross section, the four sides of the square or the rectangle may be all less than about 100 nm long. In some embodiments, a nanochannel may have a width on the surface of the substrate 105 of less than about 100 nm. In some embodiments, a nanochannel may have a depth in the substrate of less than about 100 nm. For example, a nanochannel may have cross-sectional dimensions of about 10 nm to 90 nm by about 10 nm to 90 nm, or about 30 nm by 30 nm. In some embodiments, the dimensions of a nanochannel may be specified so that a single particle of a specific type may pass through the nanochannel at a time; a nanochannel of larger dimensions may allow larger particles to flow through it.

In some embodiments, a length of a nanochannel may be about 1 micron to 200 microns. A longer nanochannel (e.g., a nanochannel having a length greater than about 50 microns) may be used for DNA stretching applications. In some embodiments, a length of a nanochannel may be about 10 microns to 30 microns. A shorter nanochannel may allow for faster flow of a liquid through the nanochannel and improved throughput.

Associated with each of the nanochannels 125 is a plasmonic nano-antenna disposed on the substrate 105. A nano-antenna is operable to localize a strong optical field at the gap of a nanochannel. A nano-antenna includes two nanostructures 140 and 145 disposed on either side of a nanochannel and proximate the nanochannel. That is, a first nanostructure 140 is disposed on a first side of the nanochannel 125 and proximate the nanochannel, and a second nanostructure 145 is disposed on a second side of the nanochannel 125 and proximate the nanochannel. In some embodiments, each of the two nanostructures 140 and 145 comprise a metal. For example, in some embodiments, each of the two nanostructures 140 and 145 comprise gold, silver, aluminum, platinum, titanium, chromium, or copper. The first and the second nanostructures 140 and 145 of the nano-antenna are operable to support plasmons; the plasmons can generate a region of high electromagnetic field intensity between the nanostructures.

In some embodiments, the two nanostructures may include strips, nanorods, bowtie-shaped structures, nanodiscs, spheres, core-shell structures, and other shapes. For example, in some embodiments, the two nanostructures 140 and 145 may each have a triangular shape. The two nanostructures 140 and 145 may be arranged so that a vertex of one triangle 140 faces a vertex of the other triangle 145. That is, in some embodiments, two nanostructures 140 and 145 may have a bow-tie shape. In some embodiments, the dimensions of each of the two nanostructures 140 and 145 substantially parallel to a surface of the substrate may be less than about 100 nm or less than about 200 nm. In some embodiments, the thickness of each of the two nanostructures 140 and 145 may be about 10 nm to 50 nm.

In some embodiments, the nanostructures 140 and 145 may be disposed on a line that passes across the nanochannel 125. In some embodiments, the line that passes across the nanochannel is substantially perpendicular to a length of the nanochannel. In some embodiments, in order for the nanostructures 140 and 145 to generate a region of high electromagnetic field intensity, the nanostructures need to be aligned on the substrate such that they are across from one another on either side of the nanochannel.

In some embodiments, each of the nanostructures 140 and 145 may be about 1 nm to 20 nm from the edges of the nanochannel 125. In some embodiments, the nanostructures 140 and 145 may be separated from one another by at least about the width of the nanochannel 125. In some embodiments, the nanostructures 140 and 145 may be less than about 100 nm or less than about 200 nm apart from one another. For example, in the case of two triangular nanostructures, the two vertices facing one another may be less than about 100 nm or less than about 200 nm apart from one another. In some embodiments, the nanostructures 140 and 145 may be separated by distance smaller than the wavelength of visible light. For example, in the case of two triangular nanostructures, the total length, along a direction substantially perpendicular to the nanochannel 125, of the two triangles and their separation (e.g., about 100 nm to 300 nm), including the nanochannel, may be smaller than the wavelength of visible light.

In some embodiments, each of the nanostructures 140 and 145 may be recessed in the surface of the substrate 105. That is, in some embodiments, the substrate may define a first nanostructure recess and a second nanostructure recess; the first nanostructure 140 may be disposed in the first nanostructure recess and the second nanostructure 145 may be disposed in the second nanostructure recess. In some embodiments, a surface of the channel defines a first plane. A surface of the first nanostructure recess and a surface of the second nanostructure recess define a second plane, with the first plane being substantially in the second plane. In some embodiments, the first and the second nanostructure recesses have a depth of about 10 nm to 100 nm or about 10 nm to 50 nm in the surface of the substrate.

The resonant spectral range of the two nanostructures can be adjusted by changing the dimensions, aspect ratio (e.g., the ratio between base and height of a triangle when the two nanostructures have a triangular shape), separation, thickness, and the metal of the two nanostructures.

In some embodiments, the optofluidic device 100 may be operable to perform single particle/molecule optical analysis with fluorescent labels (e.g., fluorescence), or without any labels (Raman or dark field scattering). Depending of the desired function of a nanochannel of the optofluidic device 100, a nanochannel may include a second nano-antenna disposed on the substrate 105. For example, to perform single molecule/particle counting, particle discrimination using fluorescent labels, particle identification and/or discrimination by Raman spectroscopy, or sequencing and/or length measurement, one nano-antenna may be associated with the nanochannel. To determine the fluid flow rate in a nanochannel or the length of an elongate particle, for example, two nano-antennas may be used.

To create a second nano-antenna, in some embodiments, a third nanostructure and a fourth nanostructure (i.e., forming a second nano-antenna) may be disposed on the substrate, with the third nanostructure being on the first side of the nanochannel and proximate the nanochannel, and the fourth nanostructure being on the second side of the nanochannel and proximate the nanochannel. In some embodiments, the third and the fourth nanostructures may be on a second line that passes across the nanochannel. In some embodiments, the third and the fourth nanostructures may be similar to the first and the second nanostructures, described above.

While the optofluidic device 100 shown in FIGS. 1 and 2 includes two nanochannels, an optofluidic device may include any number of nanochannels. In some embodiments, an optofluidic device includes one nanochannel. In some embodiments, an optofluidic device includes a plurality of nanochannels. In some embodiments, all of the nanochannels of an optofluidic device may have substantially the same dimensions (e.g., the same length and the same cross-sectional dimensions). In some embodiments, the nanochannels of an optofluidic device may have different dimensions (e.g., different lengths and/or different cross-sectional dimensions).

Methods of Fabrication

Parallel fabrication methods, low-cost processing, and low-cost materials may be used to fabricate the optofluidic devices disclosed herein. In some embodiments, an optofluidic device, including the nanochannels, is fabricated using direct nano-imprint lithography. Direct nano-imprint lithography includes thermal imprinting and UV-nano-imprinting, for example. When using UV-nano-imprinting, a hybrid inorganic-organic polymer, containing $SiO_x$ groups, may be used as an active material for the substrate. Any type of material, such as a plastic, a polymer (e.g., polycarbonate), a glass, or silicon, may be used as a substrate carrier, on which the substrate may be disposed.

In some embodiments, a metallic nano-antenna is defined by shadow evaporation of a sacrificial layer of chromium, followed by a normal evaporation of gold, and a lift-off using a chromium wet etchant. In some embodiments, an optofluidic device may be sealed by pressure bonding a cover (e.g., a plastic or a glass cover) on a surface of the optofluidic device.

Figure 3:
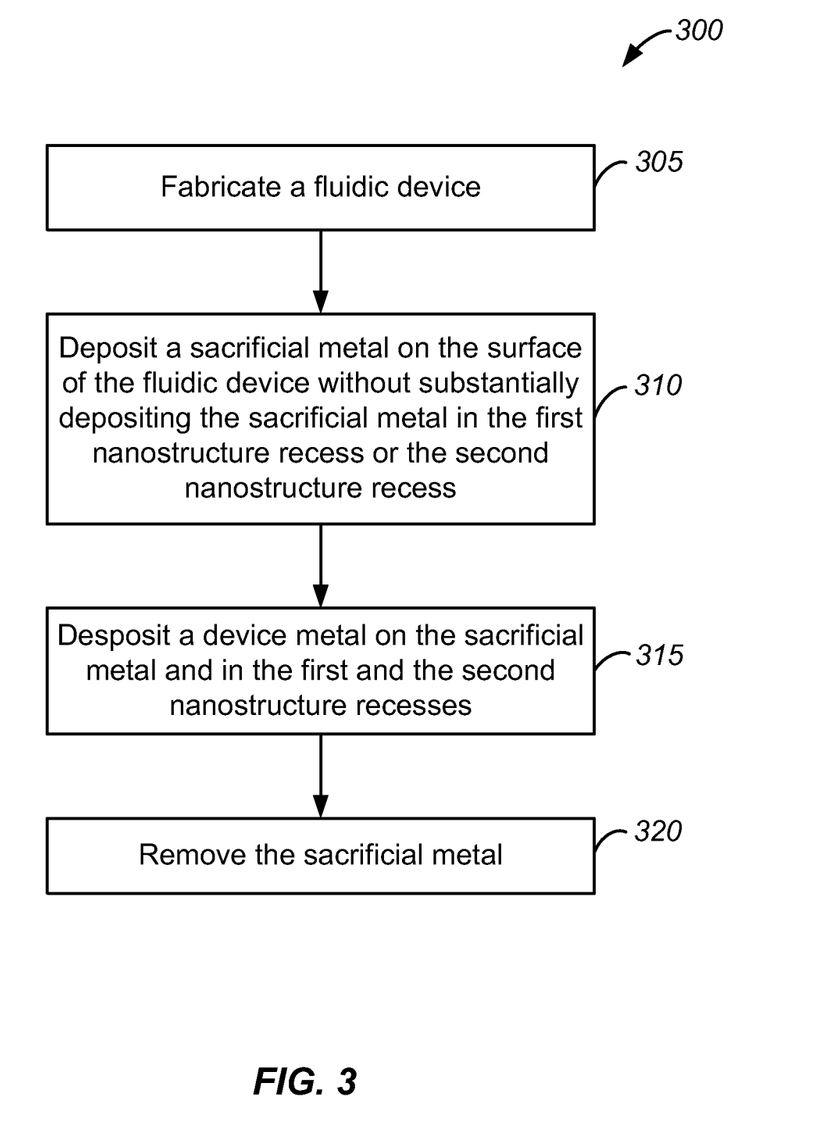
FIG. 3 shows an example of a flow diagram illustrating portions of a manufacturing process for an optofluidic device.

FIG. 3 shows an example of a flow diagram illustrating portions of a manufacturing process for an optofluidic device. FIGS. 4A-4D show examples of schematic illustrations of an optofluidic device at various stages in the manufacturing process.

Figure 4A:
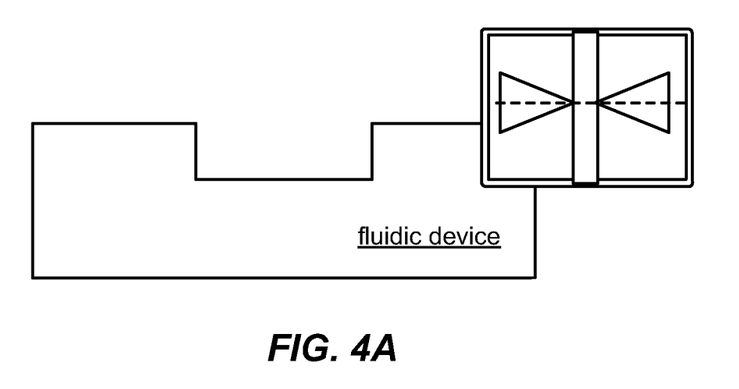
FIGS. 4A-4D show examples of schematic illustrations of an optofluidic device at various stages in the manufacturing process.

Starting at block 305 of the process 300, a fluidic device is fabricated. In some embodiments, the fluidic device has a surface defining a channel, a first nanostructure recess on a first side of the channel and proximate the channel, and a second nanostructure recess on a second side of the channel and proximate the channel. FIG. 4A shows examples a top plan view and a cross-sectional schematic illustration (i.e., through the dashed line in the top plan view) of a fluidic device.

The fluidic device may be fabricated using many different techniques. In some embodiments, ultraviolet (UV) nanoimprint lithography (NIL) is used to fabricate the fluidic device. In some embodiments, a master stamp is first fabricated. In some embodiments, a master stamp may be fabricated from a hard material (e.g., silicon or glass) using electron beam lithography (e.g., to form a nanochannel and a nanostructure recess on each side of the nanochannel), photolithography (e.g., to form microchannels and other features), and reactive ion etching. The master stamp may be used to press and form the features, including the microchannels and nanochannels, nanostructure recesses, and other structures in a polymer material.

In some embodiments, a stamp replica may be fabricated using a master stamp to use to fabricate a fluidic device, as fabricating a master stamp may be expensive and time consuming. Many stamp replicas may be fabricated from a single master stamp. In some embodiments, fabricating a stamp replica may include depositing a UV light curable polymer onto the master stamp, pressing the UV light curable polymer with a planar piece of material (e.g., glass or plastic), curing the polymer using UV light, and separating the structure from the master stamp. In some embodiments, the stamp replica may be coated with an anti-stick coating.

In some embodiments, the stamp replica may be used to fabricate the fluidic device by direct nanoimprint lithography. In some embodiments, fabricating the fluidic device may include depositing an UV light curable polymer onto the stamp replica, pressing the UV light curable polymer with a substrate carrier (e.g., glass, plastic or silicon), curing the polymer using UV light, and separating the structure from the stamp replica.

Figure 4B:
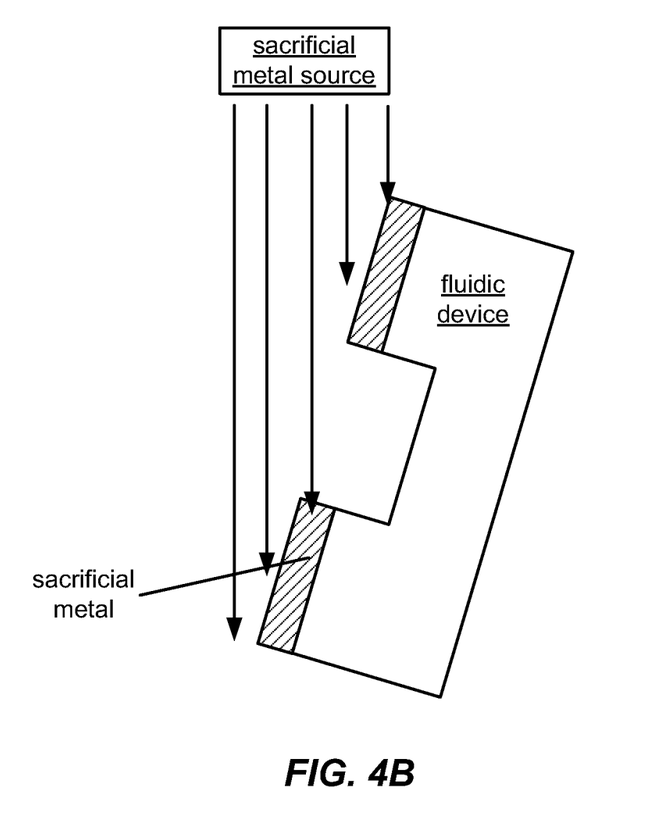

Returning to FIG. 3, at block 310 of the process 300, a sacrificial metal is deposited on the surface of the fluidic device without substantially depositing the sacrificial metal in the first nanostructure recess or the second nanostructure recess. In some embodiments, the sacrificial metal is deposited in the channel. In some embodiments, the sacrificial metal deposition may be performed using a physical vapor deposition process in which the fluidic device is positioned with respect to the sacrificial metal source such that little or no sacrificial metal is deposited in the nanostructure recesses. For example, the fluidic device may be disposed such that the surface of the fluidic device shields or blocks deposition of the sacrificial metal from being deposited in the nanostructure recesses, while the sacrificial metal is being deposited on the surface. In some embodiments, the physical vapor deposition process comprises an evaporation process. In some embodiments, the sacrificial metal comprises chromium. FIG. 4B shows an example of a cross-sectional schematic illustration of a fluidic device while block 310 is being performed.

Figure 4C:
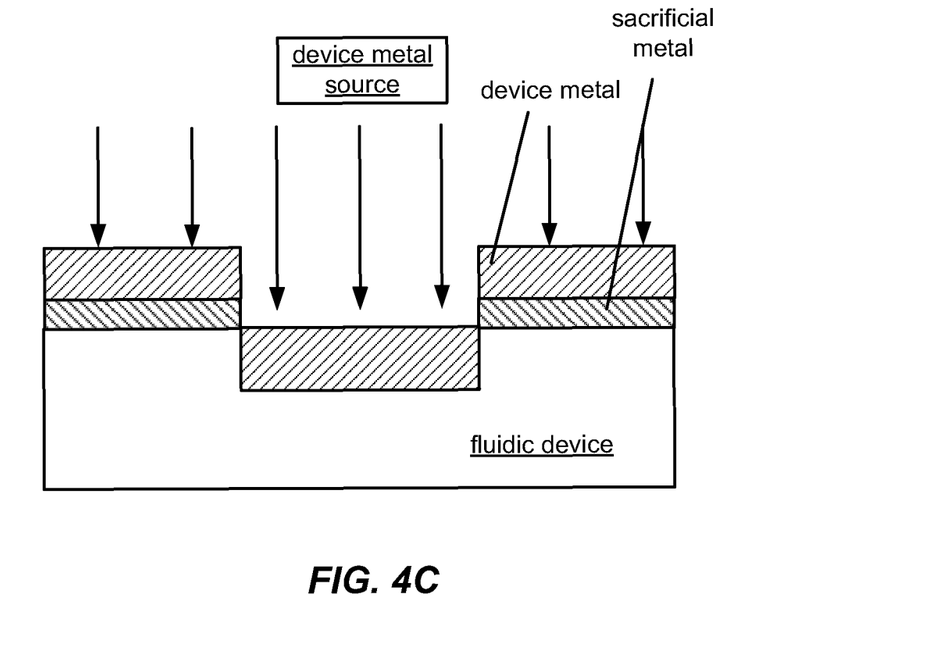

At block 315, a device metal is deposited on the sacrificial metal and in the first and the second nanostructure recesses. In some embodiments, the device metal deposition may be performed using physical vapor deposition process. In some embodiments, the physical vapor deposition process comprises an evaporation process. In some embodiments, the device metal comprises gold. FIG. 4C shows an example of a cross-sectional schematic illustration of a fluidic device while block 315 is being performed.

Figure 4D:
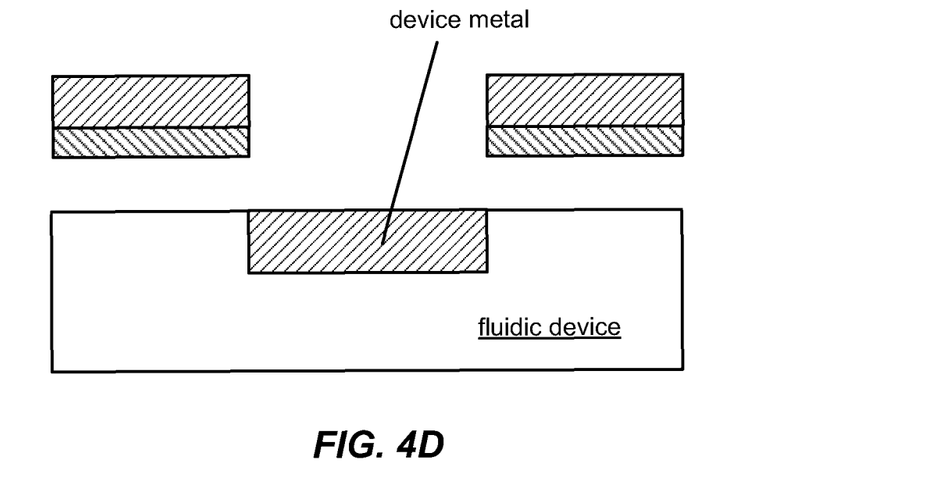

At block 320, the sacrificial metal is removed. In some embodiments, a wet etchant may be used to remove the sacrificial metal. In some embodiments, removing the sacrificial metal also removes the device metal overlaying the sacrificial metal. FIG. 4D shows an example of a cross-sectional schematic illustration of a fluidic device at this point in the optofluidic device fabrication process. As shown in FIG. 4D, the device metal is left in the nanostructure recesses after block 320.

Other operations may be performed to complete the fabrication of an optofluidic device. For example, in some embodiments, a cover may be bonded (e.g., pressure bonded) to the surface of the fluidic device.

Methods of Use

One advantage of the optofluidic devices disclosed herein is their versatility; they can be used in many different configurations and can be used to detect and identify a large number of different substances, particles, molecules, and/or biomolecules.

Figure 5:
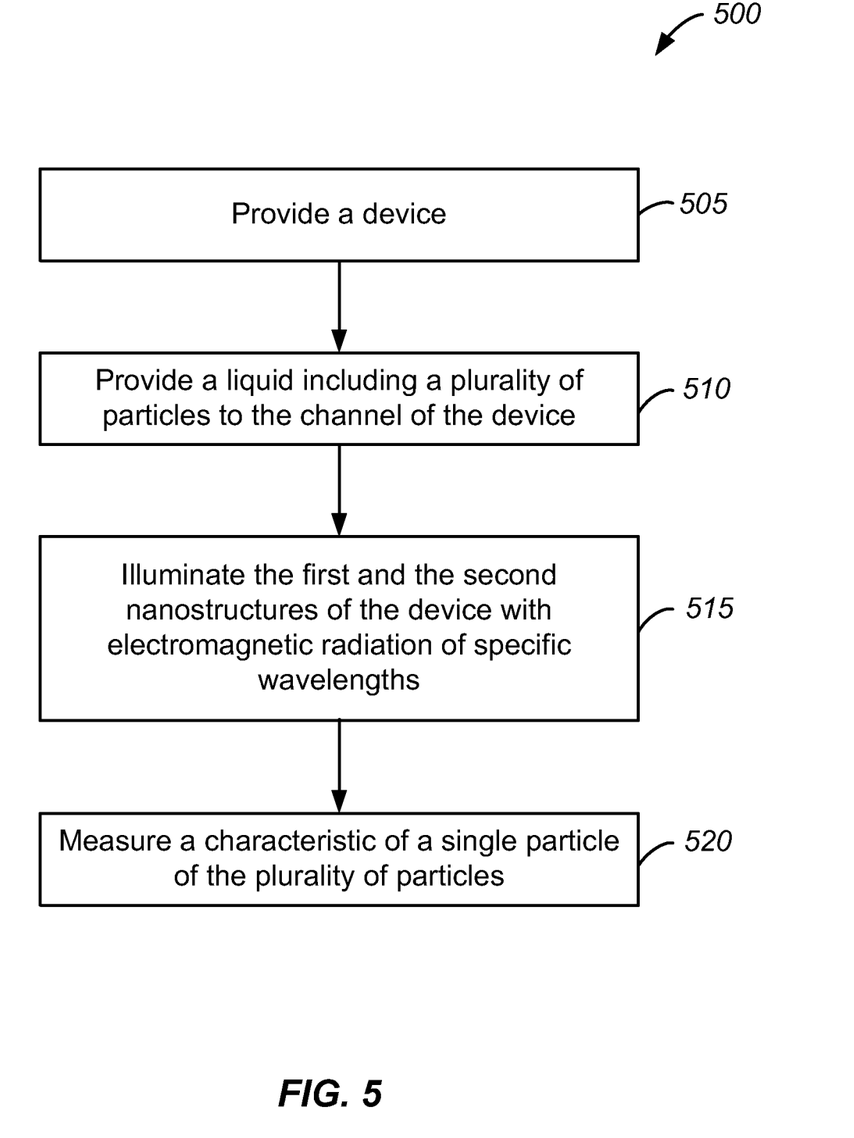
FIG. 5 shows an example of a flow diagram illustrating a method of using an optofluidic device.

An optofluidic device can be operated in many different modes, including but not restricted to dark field spectroscopy, enhanced fluorescent emission, and enhanced Raman spectroscopy. FIG. 5 shows an example of a flow diagram illustrating a method of using an optofluidic device. At block 505 of the method 500, a device is provided. The device may be any of the optofluidic devices disclosed herein. At block 510, a liquid including a plurality of particles is provided to the channel of the device. For example, microfluidic features in the device may be used to provide the liquid to the channel and to cause the liquid to flow through the channel. In some embodiments, the particles may be complex molecules, biomolecules, nanoparticles, quantum dots, or other nanostructures.

At block 515, the first and the second nanostructures of the device are illuminated with electromagnetic radiation of specific wavelengths. In some embodiments, the first and the second nanostructures of the device are illuminated with electromagnetic radiation of a specific range of wavelengths or a specific wavelength. The electromagnetic radiation may be provided by a laser, for example. A specific wavelength or range or wavelengths of the electromagnetic radiation may be tailored to the use of the optofluidic device. For example, to perform dark field spectroscopy, a broadband source (a wavelength or wavelengths of about 390 nm to 900 nm) may be used; to perform enhanced fluorescent emission, a wavelength or wavelengths of about 600 nm to 750 nm may be used; to perform enhanced Raman spectroscopy, a wavelength or wavelengths of about of 600 nm to 750 nm may be used.

At block 520, a characteristic of a single particle of the plurality of particles is measured. This is performed as the single particle flows in the channel between the first and the second nanostructures. The characteristic of the single particle is measured from the interaction of the single particle with a region of high electromagnetic field intensity between the first nanostructure and the second nanostructure. This region of high electromagnetic field intensity between the first nanostructure and the second nanostructure may be created by coupled surface plasmons in the first and second nanostructures that are induced by the electromagnetic radiation of specific wavelengths or a specific wavelength.

Experiments

The following descriptions of experiments are intended to be examples of the embodiments disclosed herein, and are not intended to be limiting.

Dark field spectroscopy with an optofluidic device can be used to investigate liquid flow at the nanoscale. Nanochannel filling, the manner in which a liquid flows, the refractive index of a sample, the polar or non-polar nature of a sample, or the composition of a liquid or a liquid mixture can be detected/measured in real time. The passage of non-labeled nanoparticles or molecules (e.g., proteins) can be detected by observing the intensity and the wavelength of the peak maximum intensity of electromagnetic radiation (e.g., visible light) at the nano-antenna; for example, the position of the maximum electromagnetic radiation at the nano-antenna may be shifted when a non-labeled nanoparticle or molecule passes through the nano-antenna.

In some experiments, the detection of about 30 zL of liquid flowing along a nanochannel, by measuring a shift in the resonance peak position (15 nm for water, 50 nm for toluene), has been shown. For the water experiments, a pre-filling state was observed, in which the peak intensity was shifted 7 nm compared to the empty channel. While not being bound to any mechanism, this was attributed to the fact that the nanochannels are first filled along the walls of a nanochannel, and then filled completely.

Enhanced fluorescent emission with an optofluidic device is based on detecting the fluorescent signal from a molecule marked with a fluorophore or a quantum dot when it passes through a nanochannel with a nano-antenna. The nano-antenna may enhance the excitation signal and the fluorophore emission several orders of magnitude, which may allow for the reduction of the necessary excitation intensity and may allow for real-time observation due to the short integration time required to see the signal (e.g., it is not necessary to immobilize the molecules). A nano-antenna may also make possible the observation of single, individual molecules, independent of their concentration (e.g., low concentration or high concentration) due to the confinement/enhancement of the signal at and coming from the nano-antenna gap. For example, this may mean that the signal from molecules passing along a 30 nm by 30 nm gap may be magnified and observed, one molecule at a time.

With a technique where the signal from the fluorophores is detected without a nano-antenna, the technique would be limited by the size of the laser spot (e.g., the diameter of which is typically in the micron range). Overlapping signal from several molecules would be detected at the same time which would not be able to be discriminated.

Experiments have been performed with embodiments of an optofluidic device as disclosed herein. In these experiments, single quantum dots (e.g., about 15 nm in diameter) passing along a nanochannel of the optofluidic device were observed one-by-one when the photoluminescence signal was magnified by the nano-antenna of the optofluidic device. To perform these experiments, the laser spot was in a fixed position and the fluorescence intensity was recorded for a period of time. The passage of each quantum dot was observed as a peak in the fluorescence intensity.

Enhanced Raman spectroscopy with an optofluidic device may allow for the measurement of the vibrational spectra of each molecule passing along the gap (i.e., a "molecule fingerprint") in such a way that it may be possible to detect, identify, and count them without using labels. The excitation signal (e.g., a laser) may be enhanced by the nano-antenna. The Raman scattering may also be magnified by the nano-antenna. The experiment can be made to match both the excitation and the emitted signals to have a squared global enhancement, which can be as high as about $10^{11}$ times the raw signal.

In some experiments, it was shown that a nano-antenna can enhance the Raman scattering signal from a polymeric substrate, as well as from non-confined liquids (e.g., such as ethanol or isopropanol) dropped onto an optofluidic device not having a cover.

In addition to the detection of single molecules by enhanced florescence or Raman spectroscopy, an optofluidic device can be operated in other modes. For example, the length of a specific molecule also can be measured if the flow rate is known. Also, two nano-antennas can be placed along the same nanochannel so that flow rates can be measured. Alternatively, two nano-antennas can be spaced a certain distance apart, and the length of a particle or molecule and the flow rate can be determined. This may be of use for determining the length of DNA fragments or other long molecules. As another example of use, DNA fragments or molecules can be locally marked with a certain fluorophore or quantum dot at a specific point or matching a specific sequence, in such a way that the fluorescent sequence can be obtained and the particular genomic information can be determined.

Figure 6A:
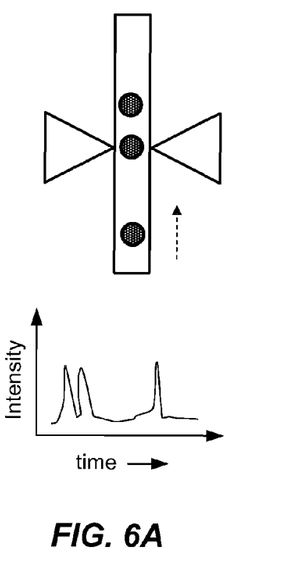
FIGS. 6A-6F show examples of schematic illustrations of an optofluidic device in operation and results that may be generated.
Figure 6B:
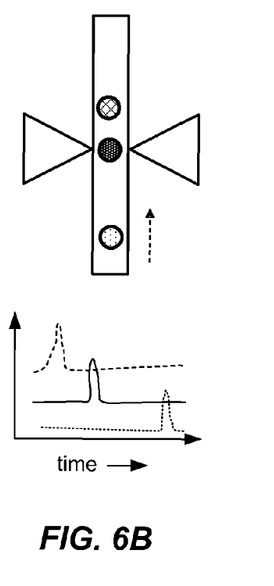
Figure 6C:
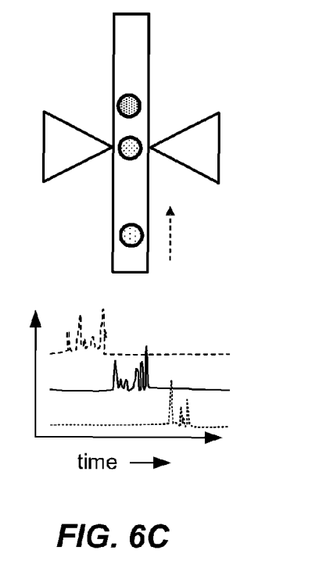
Figure 6D:
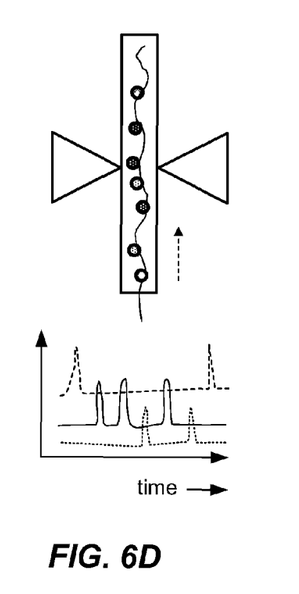
Figure 6E:
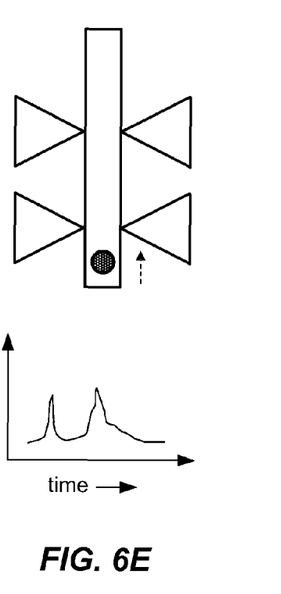
Figure 6F:
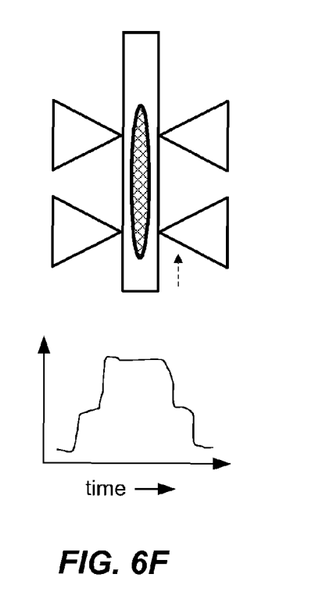

FIGS. 6A-6F show examples of schematic illustrations of an optofluidic device in operation and results that may be generated. FIG. 6A shows an example of single molecule/particle counting. FIG. 6B shows an example of particle discrimination using fluorescent labels. FIG. 6C shows an example of particle identification and/or discrimination by Raman spectroscopy. FIG. 6D shows an example of sequencing and/or length measurement. FIG. 6E shows an example of the determination of fluid flow rate in a nano-channel using two nano-antennas. FIG. 6F shows an example of measuring the length of an elongate particle, which may be performed with one nano-antenna or two nano-antennas.

Embodiments disclosed herein allow for the detection, discrimination, and quantification of very low amounts of substances, including single particles and single (bio)molecules, for example. One advantage of the devices and methods is that they may be used to create a wide range of unique biosensors; e.g., the analysis of single molecules can be used to detect, identify, and/or discriminate blood/saliva biomarkers, lipids, proteins, genetic material, virus, virus-like particles, explosives, toxins, pollutants, etc. Some further applications may include: the environmental monitoring of biotoxins, such as mycrocistins, in fresh water (e.g., this could be a powerful method to detect algae blooms at an early stage); in-line tap water quality monitoring; the detection and identification of virus infections for home analysis; and the detection and identification of virus infections for medical analysis.

CONCLUSION

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A device comprising:
   a substrate comprising a polymer;
   a channel having cross-sectional dimensions of less than about 100 nanometers defined in a surface of the substrate;
   a first nanostructure and a second nanostructure, the first and the second nanostructures comprising a metal, the first nanostructure disposed on the substrate on a first side of the channel and proximate the channel, the second nanostructure disposed on the substrate on a second side of the channel and proximate the channel, the first and the second nanostructures disposed on a line that passes across the channel, and dimensions of the first and the second nanostructures substantially parallel to the surface of the substrate being less than about 200 nanometers, the first and the second nanostructures being operable to support surface plasmons that resonate and generate a region of high electromagnetic field intensity between the first nanostructure and the second nanostructure; and
   a cover comprising the polymer or a glass disposed on the surface of the substrate, the channel being defined by the substrate and the cover.

2. The device of claim 1, wherein the substrate further defines a first nanostructure recess and a second nanostructure recess in the surface of the substrate, wherein the first nanostructure is disposed in the first nanostructure recess, and wherein the second nanostructure is disposed in the second nanostructure recess.

3. The device of claim 2, wherein the first and the second nanostructure recesses have a depth of about 10 nanometers to 100 nanometers in the surface of the substrate.

4. The device of claim 1, wherein the line that passes across the channel is substantially perpendicular to a length of the channel.

5. The device of claim 1, further comprising:
   a third nanostructure and a fourth nanostructure disposed on the substrate, wherein the third nanostructure is on the first side of the channel and proximate the channel, wherein the fourth nanostructure is on the second side of the channel and proximate the channel, and wherein the third nanostructure and the fourth nanostructure are on a second line that passes across the channel.

6. The device of claim 1, wherein the first and the second nanostructures comprise a metal selected from the group consisting of gold, silver, aluminum, platinum, titanium, chromium, and copper.

7. The device of claim 1, wherein the first nanostructure is positioned about 1 nanometer to 20 nanometers from the first side of the channel, and wherein the second nanostructure is positioned about 1 nanometer to 20 nanometers from the second side of the channel.

8. The device of claim 1, wherein the channel has a width on the surface of the substrate of less than about 100 nanometers, and wherein the first and the second nanostructures are separated by at least the width of the channel.

9. The device of claim 1, wherein the channel has a depth in the substrate of less than about 100 nanometers.

10. The device of claim 1, wherein a length of the channel is about 1 micron to 200 microns.

11. The device of claim 1, further comprising:
a second channel defined in the surface of the substrate and coupled to the channel, wherein the cover defines a hole, and wherein the hole is coupled to the second channel and provides an inlet for a liquid to the device.

12. The device of claim 1, further comprising:
a second channel defined in the surface of the substrate and coupled to the channel, wherein the substrate defines a hole, and wherein the hole is coupled to the second channel and provides an inlet for a liquid to the device.

13. A device comprising:
a substrate;
a channel having cross-sectional dimensions of less than about 100 nanometers defined in a surface of the substrate;
a first nanostructure and a second nanostructure, the first and the second nanostructures each comprising a nanorod, the first nanostructure disposed on the substrate on a first side of the channel and proximate the channel, the second nanostructure disposed on the substrate on a second side of the channel and proximate the channel, the first and the second nanostructures disposed on a line that passes across the channel, and dimensions of the first and the second nanostructures substantially parallel to the surface of the substrate being less than about 200 nanometers, the first and the second nanostructures being operable to support surface plasmons that resonate and generate a region of high electromagnetic field intensity between the first nanostructure and the second nanostructure; and
a cover disposed on the surface of the substrate.

14. The device of claim 13, wherein the cover comprises a polymer or a glass.

15. The device of claim 13, wherein the first and the second nanostructures comprise a metal.

16. The device of claim 13, wherein the substrate comprises a polymer.

* * * * *